(12) United States Patent
Tzeng

(10) Patent No.: US 6,750,223 B2
(45) Date of Patent: Jun. 15, 2004

(54) 4-ANILINO[2,3-B]QUINOLINE DERIVATIVES, THEIR PREPARATION PROCESSES AND PHARMACEUTICAL COMPOSITIONS COMPRISING THE SAME

(75) Inventor: Cherng-Chyi Tzeng, Kaohsiung (TW)

(73) Assignee: Kaohsiung Medical University, Kaohsiung (TW)

( * ) Notice: Subject to any disclaimer, the term of this patent is extended or adjusted under 35 U.S.C. 154(b) by 0 days.

(21) Appl. No.: 10/241,740

(22) Filed: Sep. 12, 2002

(65) Prior Publication Data

US 2004/0072856 A1 Apr. 15, 2004

(51) Int. Cl.$^7$ ............... A61K 31/44; C07D 471/00; C07D 491/00
(52) U.S. Cl. ............ 514/291; 514/292; 546/84; 546/89; 546/92
(58) Field of Search .............. 546/84, 89, 92; 514/292, 291

(56) References Cited

U.S. PATENT DOCUMENTS

| | | |
|---|---|---|
| 2,650,229 A | 8/1953 | Timmler et al. ............ 546/89 |
| 3,631,050 A | 12/1971 | Elslager et al. ............ 546/64 |
| 5,202,440 A * | 4/1993 | Desai ............ 546/89 |
| 5,208,330 A * | 5/1993 | Shutske et al. ............ 540/471 |

* cited by examiner

*Primary Examiner*—D. Margaret Seaman
*Assistant Examiner*—Raymond Covington
(74) *Attorney, Agent, or Firm*—Baker Botts L.L.P.

(57) ABSTRACT

Disclosed herein are 4-anilino[2,3-b]quinoline derivatives of formula (I):

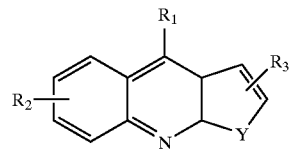

wherein each of $R_1$, $R_2$, $R_3$ and Y is given the definition as set forth in the Specification and Claims. These compounds of formula (I) have been found to have the ability to inhibit growth of a variety of tumor/cancer cells, especially leukemia, colon, melanoma and breast cancer cells.

Also, disclosed are preparation processes of these compounds of formula (I) and pharmaceutical compositions comprising said compositions of formula (I).

29 Claims, No Drawings

4-ANILINO[2,3-B]QUINOLINE DERIVATIVES, THEIR PREPARATION PROCESSES AND PHARMACEUTICAL COMPOSITIONS COMPRISING THE SAME

BACKGROUND OF THE INVENTION

1. Field of the Invention

The present invention relates to novel 4-anilino[2,3-b]quinoline derivatives, which are found to have the ability to inhibit the growth of a variety of tumor/cancer cells, especially leukemia, colon, melanoma, and breast cancer cells, and the preparation processes of these derivatives, and their uses in the manufacture of pharmaceutical compositions.

2. Description of the Related Art

Acridine derivatives, especially 9-anilinoacridines, have been extensively studied as potential chemotherapeutic agents due to their capability of intercalating DNA leading to the inhibition of mammalian topoisomerase II (Atwell, G. J. et. al., *J. Med. Chem.* 1972, 15, 611–615; Denny, W. A. et. al., *J. Med. Chem.* 1978, 21, 5–10; Denny, W. A. et. al., *J. Med. Chem.* 1982, 25, 276–315; Gamage, S. A. et. al., *J. Med. Chem.* 1994, 37, 1486–1494; Gamage, S. A. et. al., *J. Med. Chem.* 1997, 40, 2634–2642). 4'-(9-acridinylamino)methanesulfonyl-m-anisidine (amsacrine, m-AMSA) is reported to be specifically relevant and has become a useful clinical drug for the treatment of leukemia and lymphoma (Atwell, G. J. et. al., *J. Med. Chem.* 1972, 15, 611–615).

A tremendous amount of effort has been directed toward the design and preparation of new amsacrine analogues with the aim of developing new drug candidates with an improved broad spectrum of antitumor activity (Baguley, B. C. et. al., *J. Med. Chem.* 1981, 24, 520–525; Rewcastle, G. W. et. al., *J. Med. Chem.* 1986, 29, 472–477; Denny, W. A. et. al., *J Med. Chem.* 1987, 30, 658–663; Su, T. L. et. al., *J. Med. Chem.* 1995, 38, 3226; Stanslas, J. et. al., *J. Med. Chem.* 2000, 43, 1563–1572).

For example. 3-(acridin-9-ylamino)-5-(hydroxymethyl)aniline (AHMA) was reported to be superior to m-AMSA against the growth of certain solid tumors, such as mammary adenocarcinoma, melanoma, and Lewis lung carcinoma in mice. Unlike m-AMSA, AHMA, which has a 3,5-disubstituted anilino moiety, was resistant to the oxidative metabolism and, therefore, was expected to have longer half-life in plasma. (T. L. Su, T. C Chou, J. Y. Kim, J. T. Huang, G. Ciszewska, W. Y. Ren, G. M. Otter, F. M. Sirotnak, K. A. Watanabe, *J. Med. Chem.* 1995, 38, 3226).

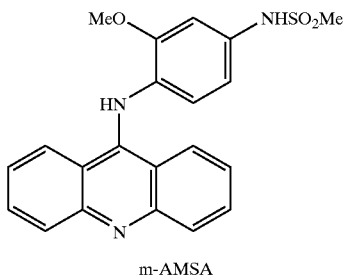

m-AMSA

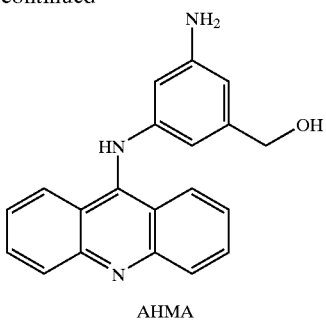

AHMA

However, the above-mentioned studies focused only on the 9-anilinoacridine skeleton, with a wide variety of substituents on anilino- and/or acridine chromophore. No attempt has been carried out concerning the replacement of acridine with its isosteric furo[2,3-b]quinoline ring which constitutes an important group of bioactive natural products, such as dictamnine, robustine, and haplopine (Chen, I. S. et. al., *Phytochemistry* 1994, 36, 237–239; Zhao, W. et. al., *Phytochemistry* 1998, 47, 7–11).

SUMMARY OF THE INVENTION

Therefore, in the first aspect of this invention, the present invention provides novel 4-anilino[2,3-b]quinoline derivatives of formula (I):

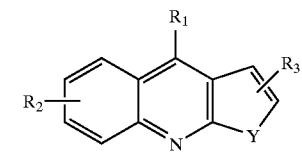

wherein

Y represents: S, O or NH $R^1$ represents a group selected from the group consisting of:

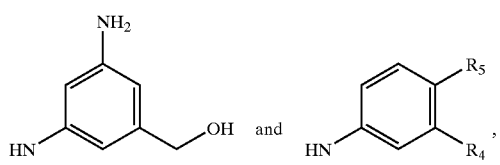

wherein $R^4$ represents: H or

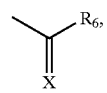

wherein X represents O, S, NH or NOR, R in NOR being H or a $C_1$–$C_4$ alkyl group, and $R_6$ represents H or a $C_1$–$C_4$ alkyl group;

$R_5$ is selected from the group consisting of H,

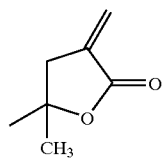

and

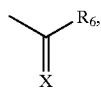

wherein X represents O, S, NH or NOR, R in NOR being H or a $C_1$–$C_4$ alkyl group, and $R^6$ represents H or a $C_1$–$C_4$ alkyl group;

with the proviso that one of $R_4$ and $R_5$ is H;

$R_2$ represents: H, halogen, a $C_1$–$C_4$ alkyl group, hydroxyl, a $C_1$–$C_4$ alkoxy group, nitro or amino; and $R_3$ represents: H, halogen, a $C_1$–$C_4$ alkyl group, hydroxyl, a $C_1$–$C_4$ alkoxy group, nitro or amino.

In the second aspect, the present invention provides a pharmaceutical composition which comprises the above-described derivative, in its free type or a pharmaceutically acceptable salt thereof, as an active ingredient in inhibiting the growth of tumor/cancer cells, especially leukemia, colon, melanoma, and breast cancer cells.

In the third aspect, the present invention provides processes for preparing the above-described derivatives of formula (I), as well as their intermediate compounds.

In particular, the present invention provides processes for preparing a compound of formula (I')

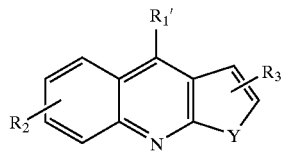

wherein

Y represents: S, O or NH;

$R^1$ represents a group selected from the group consisting of:

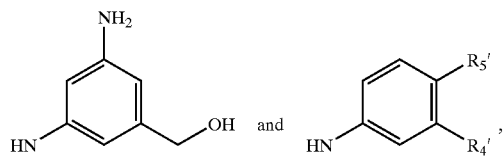

wherein one of $R_4'$ and $R_5'$ is H, and the other is

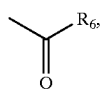

wherein $R_6$ represents H or a $C_1$–$C_4$ alkyl group;

$R_2$ represents: H, halogen, a $C_1$–$C_4$ alkyl group, hydroxyl, a $C_1$–$C_4$ alkoxy group, nitro or amino; and $R_3$ represents: H, halogen, a $C_1$–$C_4$ alkyl group, hydroxyl, a $C_1$–$C_4$ alkoxy group, nitro or amino;

the process comprising the step of reacting a compound of formula (A):

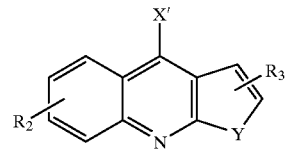

wherein $R_2$, $R_3$ and Y are the same as those defined for formula (I'); and

X' represents Cl, Br or I;

with a compound selected from the group consisting of a compound of formula

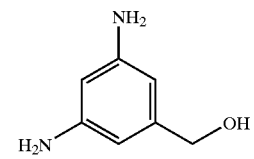

and a compound of formula

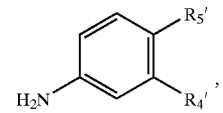

wherein $R_4'$ and $R_5'$ are the same as those defined for formula (I').

The above and other objects, features and advantages of the present invention will become apparent with reference to the following detailed description of the preferred examples.

DETAILED DESCRIPTION OF THE INVENTION

The applicant noted that furo[2,3-b]quinoline system possesses a higher electron density than that of acridine systems and, therefore, is advantageous, since the major route of breakdown for m-AMSA in vivo is a non-enzymatically mediated attack of thiol at C(9), which would eventually result in loss of the side chain and the formation of inactive products (B. F. Cain, W. R. Wilson, B. C. Baguley, *Mol. Pharmacol.* 1976, 12, 1027; W. R. Wilson, B. F. Cain, B. C. Baguley, *Chem.-Biol. Interact.*, 977, 18, 163; and R. L. Cysyk, D. Shoemaker, R. H. Adarnson, *Drug Metab. Dispos.* 1977, 5, 579).

In earlier researches, the applicant synthesized certain α-methylindene-γ-butyrolactone-bearing quinolones and evaluated their cytotoxicities on the ground that, through the intercalation of quinolone, the α-methylidene-γ-butyrolactone can specifically alkylate DNA molecule (K. C. Fang, Y. L. Chen, J. Y. Sheu, T. C. Wang, C C. Tzeng, *J. Med. Chem.* 2000, 43, 3809; C. C. Tzeng, K. H. Lee, T. C. Wang, C. H. Han, Y. L. Chen, *Pharmaceut. Res.* 2000. 17, 715; and S. L. Hsu, Y. L. Chen, K. C. Fang, J. Y. Sheu, C. C. Tzeng, *Helv. Chim. Acta* 2001, 84, 874). This versatile α-methylidene-γ-butyrolactone moiety is appended on the 9-anilino group (see compound 6 shown in the following synthesis scheme I) in an attempt to prepare a bifunctional compound in which the furo[2,3-b]quinoline moiety acts as an intercalator while the lactone ring plays the role of an alkylating unit.

Based on the above, the applicant further developed new bioisosteric isomers of AHMA, i.e. compounds of formula (I) or pharmaceutically acceptable salts thereof:

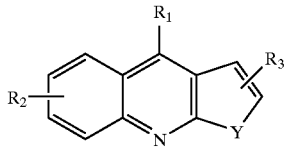

I wherein
Y represents: S, O or NH;
$R_1$ represents a group selected from the group consisting of:

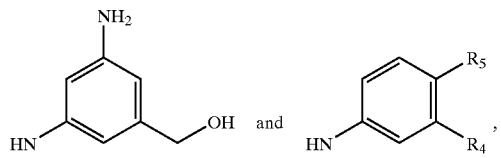

wherein
$R_4$ represents: H or

wherein X represents O, S, NH or NOR, R in NOR being H or a $C_1$–$C_4$ alkyl group, and $R_6$ represents H or a $C_1$–$C_4$ alkyl group;
$R_5$ is selected from the group consisting of H,

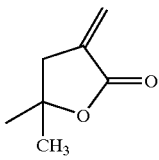

and

wherein X represents O, S, NH or NOR, R in NOR being H or a $C_1$–$C_4$ alkyl group, and $R_6$ represents H or a $C_1$–$C_4$ alkyl group;
with the proviso that one of $R_4$ and $R_5$ is H;
$R_2$ represents: H, halogen, a $C_1$–$C_4$ alkyl group, hydroxyl, a $C_1$–$C_4$ alkoxy group, nitro or amino; and
$R_3$ represents: H, halogen, a $C_1$–$C_4$ alkyl group, hydroxyl, a $C_1$–$C_4$ alkoxy group, nitro or amino.
Preferably, Y is O.
Preferably, $R_2$ is H.
Preferably, $R_3$ is H.

Preferably, $R_1$ is selected from the group consisting of

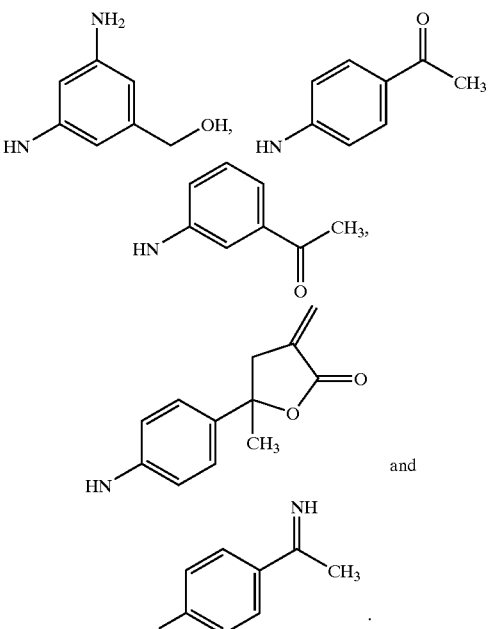

and

In a preferred embodiment, $R_1$ is

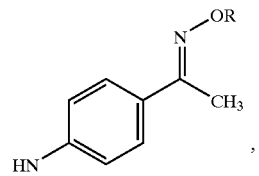

wherein R is H or methyl.
In another preferred embodiment, $R_1$ is

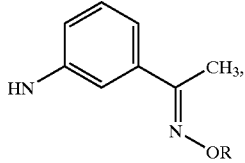

wherein R is H or methyl.

Specifically, the applicant synthesized certain mono-substituted 4-anilinofuro[2,3-b]quinoline derivatives, in which the anilino moiety thereof is substituted, at either the C(3') or C(4') position, with an Ac group as well as its corresponding oxime and methyloxime. It is expected that these substituents would form H-bonding with a DNA molecule during the intercalation process of the tricyclic furo[2,3-b]quinoline moiety with the DNA molecule.

The compounds of formula (I) according to this invention have been found to exhibit inhibitory activities against the growth of a variety of tumor/cancer cells, especially leukemia, colon, melanoma, and breast cancer cells. Therefore, the present invention also envisions the application of the compounds of formula (I) of this invention in the manufacture of pharmaceutical compositions.

According to this invention, there is provided a pharmaceutical composition comprising a therapeutically effective amount of the 4-anilino[2,3-b]quinoline derivatives described above, or a pharmaceutically acceptable salt thereof.

As used herein, the pharmaceutically acceptable salts include salts with inorganic acids, such as hydrochloride, hydrobromide, sulfate and phosphate; those with organic acids, such as acetate, maleate, tartrate, methanesulfonate; and those with amino acids, such as arginine, aspartic acid and glutamic acid.

The compounds of the present invention may also be present as a hydrate or as a stereoisomer. Therefore, it is contemplated that these hydrates and stereoisomers fall within the technical concept of the present invention.

Optionally, the pharmaceutical composition according to this invention may additionally comprise a pharmaceutically acceptable carrier widely employed in the art for the manufacture of medicaments. For example, the pharmaceutically acceptable carrier can include one or more than one of the following reagents: solvents, disintegrating agents, binders, excipients, lubricants, absorption delaying agents and the like.

The pharmaceutical composition according to this invention may be administered parenterally or orally in a suitable pharmaceutical form. Suitable pharmaceutical forms include sterile aqueous solutions or dispersions, sterile powders, tablets, troches, pills, capsules, and the like.

In addition, the active compounds of the present invention may be incorporated into sustained-release preparations and formulations. Optionally, the pharmaceutical composition according to this invention may be administered alone or in conjunction with an additional anticancer agent, such as such as Mitomycin, Adriamycin, Actinomycin, cis-platin and the like.

The new compounds of formula (I) may be prepared according to the following reaction schemes and protocols.

According to this invention, there is provided a method for producing a compound of formula (I'):

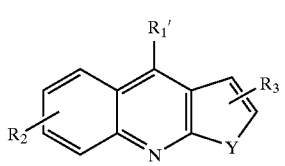

wherein
Y represents: S O or NH;
$R_1'$ represents a group selected from the group consisting of:

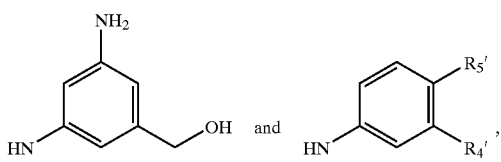

wherein one of $R_4'$ and $R_5'$ is H, and the other is

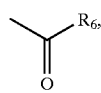

wherein $R_6$ represents H or a $C_1$–$C_4$ alkyl group;
$R_2$ represents: H, halogen, a $C_1$–$C_4$ alkyl group, hydroxyl, a $C_1$–$C_4$ alkoxy group, nitro or amino; and
$R_3$ represents: H, halogen, a $C_1$–$C_4$ alkyl group, hydroxyl, a $C_1$–$C_4$ alkoxy group, nitro or amino;

the process comprising the step of reacting a compound of formula (A):

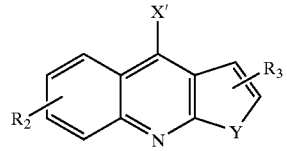

wherein
$R_2$, $R_3$ and Y are the same as those defined for formula (I'); and
X' represents Cl, Br or I; with a compound selected from the group consisting of a compound of formula

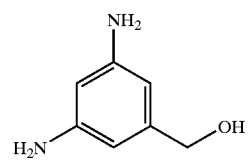

and a compound of formula

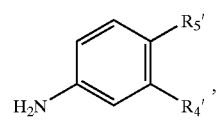

wherein $R_4'$ and $R_5'$ are the same as those defined for formula (I'). In a preferred embodiment, the used compound of formula (A) is reacted with a compound of formula

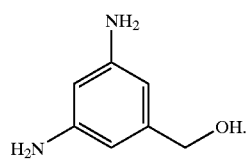

In a further preferred embodiment, the compound of formula (A) is reacted with the compound of formula

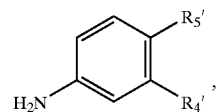

preferably

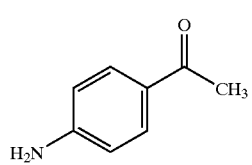

(p-aminoacetophenone) or

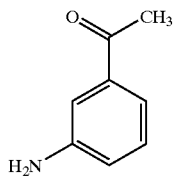

(m-aminoacetophenone). These aminoacetophenones may be chemically modified according to the prior methods, such as the method disclosed in Doud, et al. *J Am. Chem. Soc.* 1958, 80, 2205–2210, so that the methyl group present thereon is replaced by a larger alkyl group (e.g. a $C_2$–$C_4$ alkyl group).

Optionally, when the compound of formula

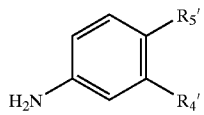

is used, the resultant compound of formula (I') may be further treated with a compound of formula $NH_2OR$, wherein R is H or a $C_1$–$C_4$ alkyl group, such that the

group in the

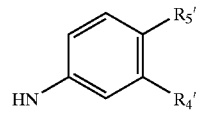

group of said compound of formula (I') is chemically modified to a

group.

The compound of formula $NH_2OR$ may be prepared, e.g. according to the following prior method:

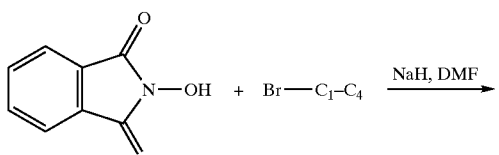

(Kim, J. N. et al., *Synth. Commun.*, 1992, 22, 1427–1432).

Alternatively, the resultant compound of formula (I') may be treated with hydroxylamine, such that the

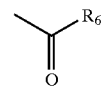

group in the

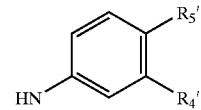

group of said compound of formula (I') is chemically modified to a

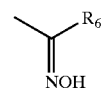

group, followed by treating the thus chemically modified compound of formula (I') with a $C_1$–$C_4$ alkyl halide, such that the

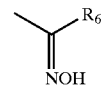

group is chemically modified to a

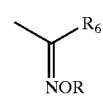

group, wherein $R_6$ is a $C_1$–$C_4$ alkyl group.

In a preferred embodiment of this invention, the compound of formula

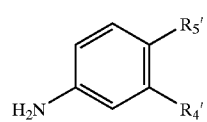

is a compound in which $R_4'$ is H and $R_5'$ is

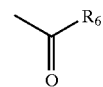

and the resultant compound of formula (I') is further treated with a compound of formula $NH_2OR$, wherein R is H or a $C_1$–$C_4$ alkyl group, such that the

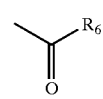

group in said compound of formula (I') is chemically modified to a

group.

In a preferred embodiment of this invention, the compound of formula

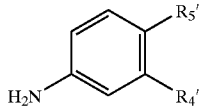

is a compound in which R4' is H and R5' is

and the resultant compound of formula (I') is further treated with ethyl 2-(bromomethyl)acrylate, such that the

group in said compound of formula (I') is chemically modified to

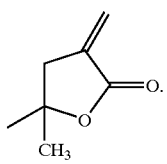

Optionally, when the compound of formula

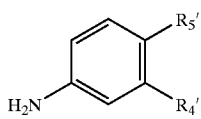

is used, the resultant compound of formula (I') may be further treated with a Lawesson's reagent or $P_2S_5$, such that the

group in the

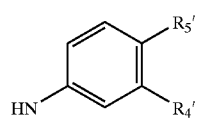

group of said compound of formula (I') is chemically modified to a

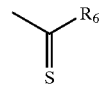

group.

The Lawesson's reagent is a commercial product available from Robinson Brothers Limited, and its chemical name is 4-methoxyphenylthiophosphine and has the following structural formula:

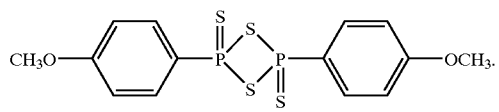

The Lawesson's reagent may be used according to the manufacturer's recommendations as posted on the internet website.

Optionally, when the compound of formula

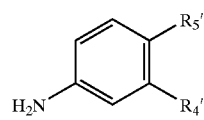

is used, the resultant compound of formula (I') may be further treated with benzyldimethylphosphinimide, such that the

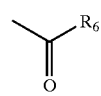

group in the

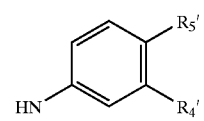

group of said compound of formula (I') is chemically modified to a

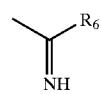

group.

Concerning the use of benzyldimethylphosphinimide in the above chemical modification, reference is made to Wannagat, U.; Muenstedt, R. *Phosphorus Sulfur*, 1987, 29, 233–238.

In a preferred embodiment of the present process, the compound of formula (A) is

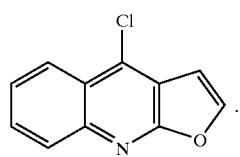

The compound of formula

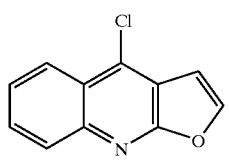

may be produced by a process comprising the steps of:

(a) forming a compound of formula

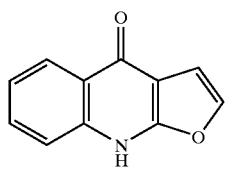

from the reaction of a compound of formula

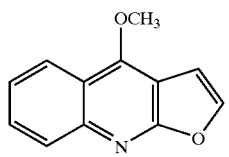

with HBr; and (b) reacting the resultant compound

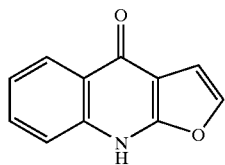

from step (a) with POCl₃.

As an alternative, the above step (b) may be carried out using POCl₃ and PCl₅, or using SOCl₂ in the presence of DMF.

In a further preferred embodiment of the present process, the compound of formula (A) is

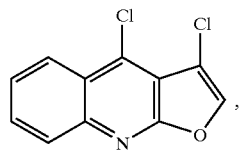

and the resultant compound of formula (I') may be further subjected to a hydrogenation reaction in the presence of Pd/C in CH₂Cl₂ to thereby form a compound of formula

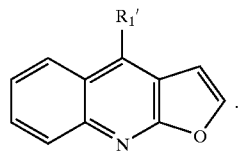

As an alternative, the above hydrogenation reaction may be carried out in the presence of NaBH₄, LiAlH₄ or Raney Ni.

The compound of formula

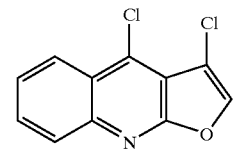

may be formed from the reaction of a compound of formula

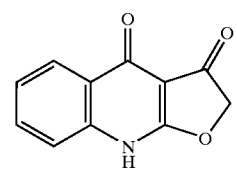

and POCl₃ (or POCl₃ and PCl₅, or SOCl₂ in the presence of DMF).

For example, when the compound of formula

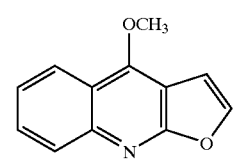

is used as the starting material, the present compound of formula (I') or (I) may be produced according to the following synthesis scheme I:

Scheme I

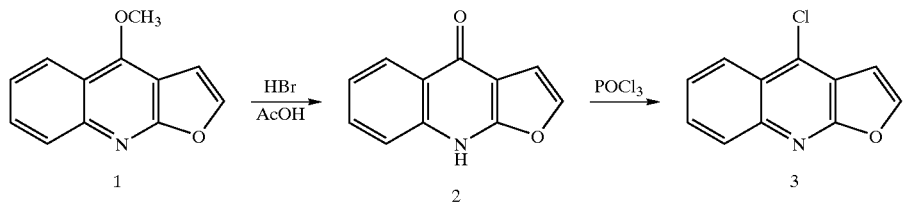

-continued
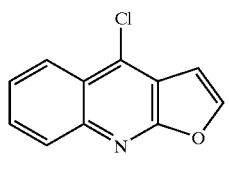
3
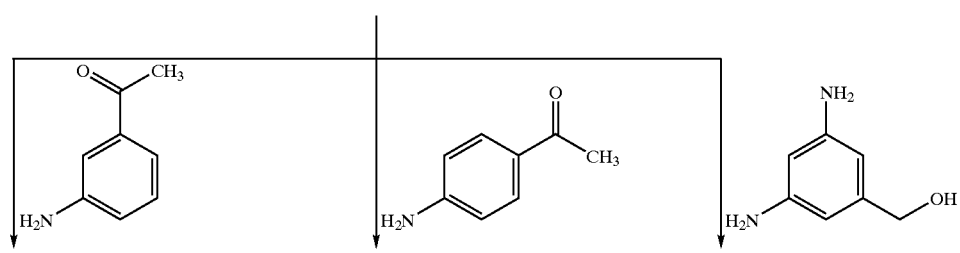
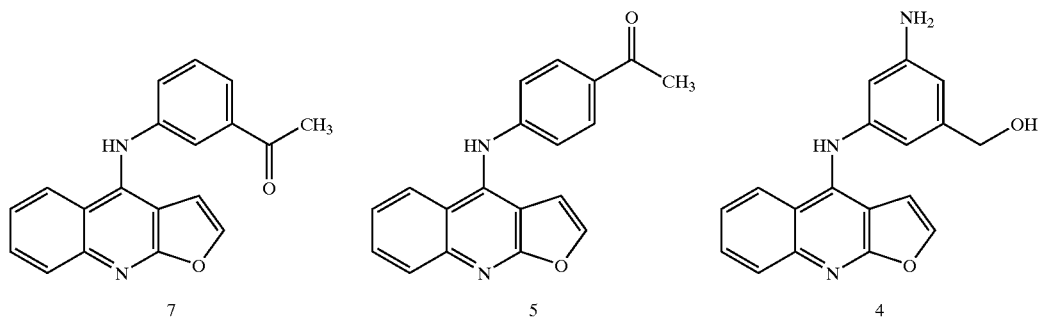
7  5  4
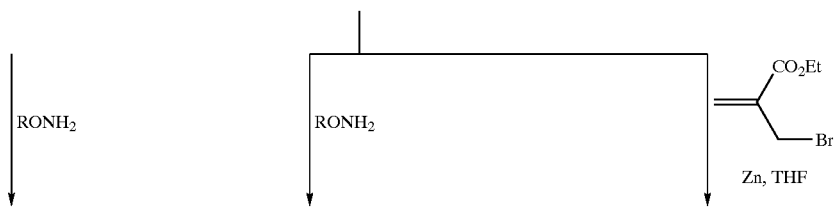
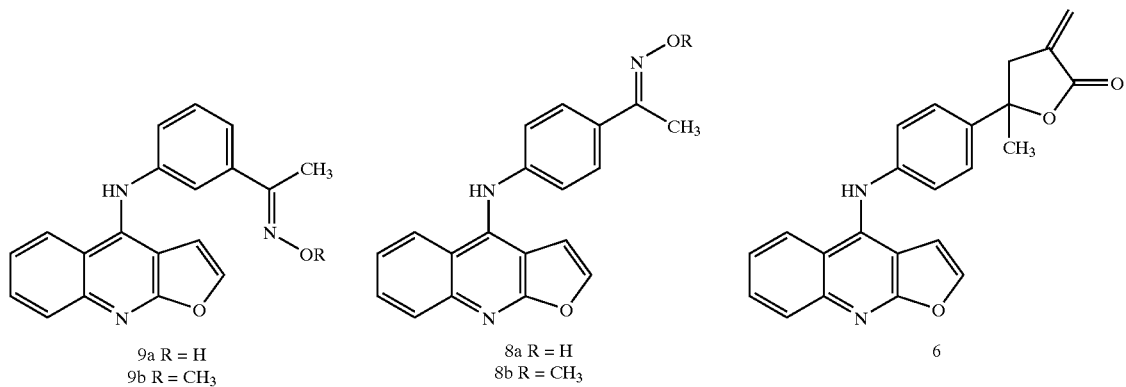
9a R = H
9b R = CH₃
8a R = H
8b R = CH₃
6

When the compound of formula

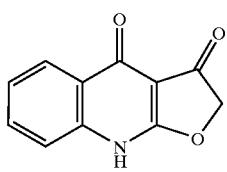

is used as the starting material, the present compound of formula (I') or (I) may be produced according to the following synthesis scheme II:

Scheme II

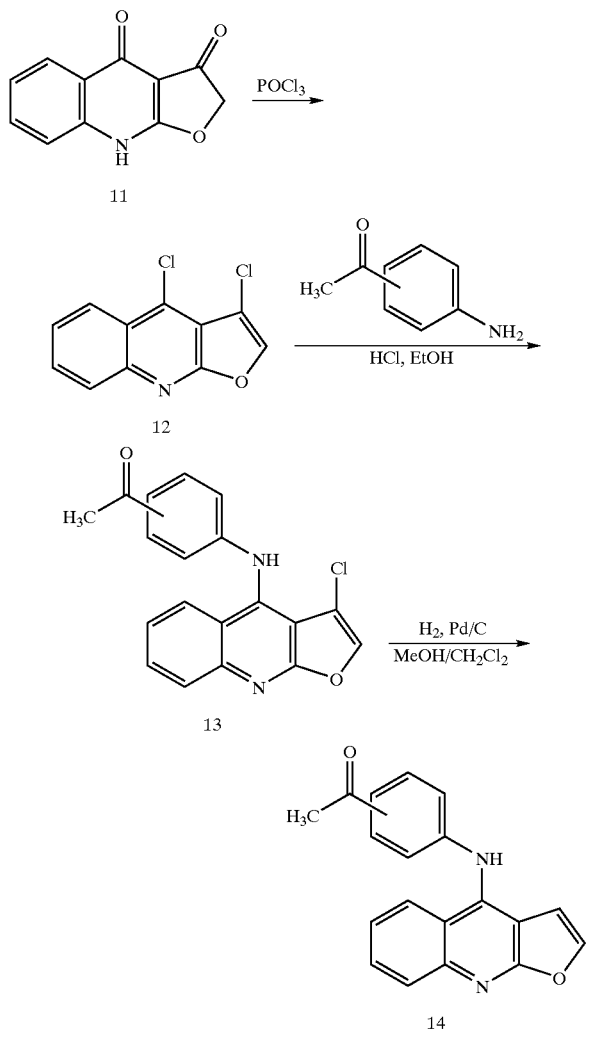

Reaction of the known substituted 2,3,4,9-tetrahydrofuro[2,3-b]quinolin-3,4-diones (compound 11) (Kuo, S. C. et. al., *J Heterocyclic Chem.*, 1991, 28, 955) with POCl$_3$ and H$_2$O (30:1) yielded the respective 3,4-dichlorofuro[2,3-b] quinolines (compound 12) which was treated with 4-aminoacetophenone in EtOH to obtain 1-[4-(3-chlorofuro [2,3-b]quinolin-4-ylamino)phenyl]ethanone (compound 13). Hydrogenation of compound 13 in the presence of Pd/C resulted in 1-[4-(furo[2,3-b]quinolin-4-ylamino)phenyl] ethanone (compound 14, corresponding to compound 5 and compound 7 in scheme I).

EXAMPLES

The following examples are given for the purpose of illustration only and are not intended to limit the scope of the present invention.

General procedures

General. TLC: precoated (0.2 mm) silica gel 60 F$_{254}$ plates from *EM Laboratories, Inc.*; detection by UV light (254 nm). M.p.: Electrothermal IA9100 digital melting-point apparatus; uncorrected. $^1$H-NMR Spectra: Varian-Unity 400 spectrometer or Varian-Gemini 200 spectrometer, chemical shifts δ in ppm with Me$_4$Si as an internal standard (=0 ppm), coupling constants J in Hz.

Elemental analyses were carried out on a Heraeus CHN-O-Rapid elemental analyzer, and results were within ±0.4% of calc. values.

Example 1.

Furo[2,3-b]quinolin-4(9H)-one (compound 2 in scheme I)

The synthesis of the title compound was carried out with reference to B. Klier, O. Schimmer, *Mutagenesis* 1999, 14, 181.

The known alkaloid, dictamnine (4-methoxyfuro[2,3-b] quinoline; compound 1 in scheme I) was isolated from the root wood of *Zanthoxylum simulans* (I. S. Chen, S. J. Wu, Y. C Lin, I. L. Tsai, H. Seki, F. N. Ko, C. M. Teng, *Phylochemistry* 1994,36, 237) and was used as the starting material.

A mixture of 4-methoxyfuro[2,3-b]quinoline (compound 1; 0.20 g, 1 mmol), 48% HBr (10 ml), and AcOH (20 ml) was refluxed for 8 h. After cooling, the mixture was poured into an ice-cold sat. NaHCO$_3$ solution (60 ml), and extracted with AcOEt (3×60 ml). The AcOEt extracts were combined, washed with H$_2$O, dried on MgSO$_4$, and evaporated to yield a residual solid, which was purified by flash column chromatography (FC; silica gel; AcOEt). The proper fractions were combined and evaporated to obtain compound 2 (0.17g, 91%).

Detected Properties of the Title Compound

M.p. 236–237° C. $^1$H-NMR (200 MHz, DMSO): 7.06 (d,J=2.4, H-C(3)) 7.29 (m,H-C(6)); 7.56–7.68 (m,H-C(2), H-C(7), H-C(8)); 8.28 (d,J)=7.6, H-C(5)). $^{13}$C-NMR (50 MHz, DMSO): 104.85; 105.84; 121.60; 122.12; 123.08; 124.60; 130.06; 140.04; 142.53; 160.70; 166.69.

The hydrolysis of compound 1 with HBr in AcOH at 110° C. for 1 h gave furo[2,3-b]quinolin-4-one (2) with 36% yield (B. Klier, O. Schimmer, *Mutagenesis* 1999, 14, 181). The yield was increased up to 91% by refluxing the reaction mixture for 8 h. This improvement is crucial because the supply of starting dictamnine could be reduced.

Example 2

4-Chlorofuro[2,3-b]quinoline (compound 3 in scheme I)

According to H. Tuppy, F. Bohm, *Monalsh. Chem.* 19S6, 87, 735, a mixture of compound 2 (0.56 g, 3 mmol), POCl$_3$ (20 ml) and Et$_3$N (2 ml) was heated at 110° C. for 8 h. The mixture was cooled to room temperature and poured into ice-H$_2$O (100 ml). A NaOH solution (6N) was added until a pH of 6 was reached. A brown precipitate thus obtained was collected and purified by FC (silica gel; CH$_2$Cl$_2$) to result in the title compound 3 (0.45 g, 73%).

Detected Properties of the Title compound

M.p. 112–113° C. $^1$H-NMR (200 MHz, DMSO): 6.99 (d,J=2.6, H-C(3)); 7.63 (m, H-C(6)); 7.77 (m, H-C(7)) 7.83 (d,J=2.6, H-C(2)); 8.15 (d,J=9.8, H-C(8)); 8.32 (m, H-C(5)). $^{13}$C-NMR (50 MHz, DMSO): 104.74; 119.29; 123.82; 124.06; 125.81; 128.80; 129.76; 134.56; 145.26; 147.37; 160.72.

Example 3

3-(Furo[2,3-b]quinolin-4-ylamino)-5-(hydroxymethyl)aniline (compound 4 in scheme I)

Compound 3 (45 mg, 0.22 mmol) and 3,5-diaminobenzyl alcohol dihydrochloride (47 mg, 0.22 mmol) were dissolved in a boiling solution of EtOH/$H_2O$ (2:1, 10 ml). Conc. HCl was added until a pH of 6 was reached, while refluxing the mixture for 40 min (TLC monitoring). The solvent was evaporated in vacuo to yield a residue, which was added into ice-$H_2O$ (20 ml) and neutralized with a 2N NaOH solution. The resultant precipitate was collected and chromatographed (silica gel; $CH_2Cl_2$/MeOH 10:1) to obtain the title compound 4 (43 mg, 64%).

Detected Properties of the Title Compound

M.p. 236–237° C. $^1$H-NMR (400 MHz, DMSO): 4.38 (d,J=5.2, $CH_2$; 5.09 (t,J)=5.2, OH); 5.18 (s, $NH_2$; 5.99 (d,J=2.4, H-C(3)); 6.33 (s, 1 arom. H); 6.40 (s, 1 arom. H); 6.45 (s, 1 arom. H); 7.44 (t,J=8.0, H-C(6)); 7.67 (t,J=8.0, H-C(7)); 7.70 (d,J=2.4, H-C(2)); 7.84 (d,J=8.4, H-C(8)); 8.42 (d,J=8.4, H-C(5)); 9.19 (s, NH). $^{13}$C-NMR (100 MHz, DMSO): 62.89; 102.87; 105.98; 107.48; 108.57; 109.53; 117.16; 122.41; 122.88; 127.90; 128.81; 141.44; 141.68; 143.44; 144.05; 145.53; 149.21; 163.03. Anal. calc. for $C_{18}H_{15}N_3O_2 \cdot 0.45H_2O$: C 68.97, H 5.11, N 13.40; found: C 69.48, H 5.10, N 13.03.

Example 4

1-[4-(Furo[2,3-b]quinolin-4-ylamino)phenyl]ethanone (compound 5 in scheme I)

The title compound 5 was synthesized according to the procedures as set forth in Example 3, except that 4-aminoacetophenone was used in place of 3,5-diaminobenzyl alcohol dihydrochloride. Compound 5 was obtained by FC (silica gel; hexane/AcOEt acetate 2:1) with 77% yield.

Detected Properties of the Title Compound

M.p. 220–221° C. $^1$H-NMR (200 MHz, $CDCl_3$): 2.59 (s, Me); 6.35 (d,J=2.6, H-C(3)); 7.11 (d,J=8.8, 2 arom. H); 7.31 (br. s, NH); 7.48 (t,J=7.4, H-C(6)); 7.57 (d,J=2.6, H-C(2)); 7.71 (t,J=8.4, H-C(7)); 7.95 (d,J=8.4, H-C(5)), H-C(8)); 8.10 (d,J =8.8, 2 arom. H). $^{13}$C-NMR (50MHz, $CDCl_3$): 26.34; 105.53; 108.73; 118.04; 119.59; 121.27; 124.37; 128.99; 129.45; 130.20; 131.36; 138.75; 143.92; 145.81; 146.15; 162–82; 196.64. Anal. calc. for $C_{19}H_{14}N_2O_2$: C 75.48, H 4.69, N 9.27; found: C 75.35, H 4.72, N 9.15.

Example 5

5-[4-(Furo[2,3-b]quinolin-4-ylamino)phenyl]-2,3,4,5-tetrahydro-5-methyl-3-methylidenefuran-2-one (compound 6 in scheme I)

The title compound 6 is produced by Reformatsky-type condensation of compound 5 with ethyl 2-(bromomethyl)acrylate in the presence of Zn powder.

To a solution of compound 5 (76 mg, 0.25 mmol) in dry THF (10 ml), activated Zn powder (22 mg, 0.32 mmol), hydroquinone (1 mg), and ethyl 2-(bromomethyl)acrylate (65 mg, 0.32 mmol) were added. The mixture was refluxed under $N_2$ for 2 h (TLC monitoring). After cooling, the mixture was poured into an ice-cold 5% HCl solution (60 ml) and extracted with $CH_2Cl_2$ (3×60 ml). The combined $CH_2Cl_2$ extracts were washed with $H_2O$, dried on $MgSO_4$, and evaporated to obtain a residual solid, which was purified by FC (silica gel; hexane/AcOEt 2:1). The proper fractions were combined and evaporated to yield a residual solid, which was recrystallized from AcOEt to result in the title compound 6 (72 mg, 78%).

Detected Properties of the Title Compound

M.p. 85–87° C. $^1$H-NMR (400 MHz, DMSO): 1.73 (s, Me); 3.24 (m, $CH_2$(4)); 5.79 (s, 1 H, $CH_2$=C(3)); 5.88 (d,J=2.0, H-C(3')); 6–12 (s, 1 H, $CH_2$=C(3)); 7.29 (d,J =8.0, 2 arom. H); 7.46 (d,J=8.0, 2 arom. H); 7.54 (m, H-C(6')); 7.77 (m, H-C(2'), H-C(7')); 7.92 (d,J =8.4, H-C(8')); 8.47 (d,J=8.4, H-C(5')); 9.80 (br. s, NH). $^{13}$C-NMR (100 MHz, DMSO): 29.12; 41.84; 83.77; 103.66; 105.76; 115.61; 117.35; 122.28; 122.75; 123.21; 123.37; 125.24; 126.47; 129.93; 135.50; 140.26; 140.47; 142.76; 143.70; 161.65; 169.10. Anal. calc. for $C_{23}H_{18}N_2O \cdot 1.2H_2O$: C 70.46, H 5.24, N 7.14; found: C70.51, H5.31, N6.91.

Example 6

1-[3-(Furo[2,3-b]quinolin-4-ylamino)phenyl]ethanone (compound 7 in scheme I)

The title compound 7 was synthesized according to the procedures as set forth in Example 3, except that 3-aminoacetophenone (available from Lancater Synthesis Ltd.) was used in place of 3,5-diaminobenzyl alcohol dihydrochloride. The crude product was recrystallized from AcOEt to result in compound 7 with 91% yield.

Detected Properties of the Title Compound

M.p. 158–159° C. $^1$H-NMR (400 MHz, DMSO): 2.57 (s, Me); 6.03 (d,J=2.4, H-C(3)); 7.49 (m, 2 arom. H, and H-C(6)); 7.74 (m, 2 arom. H, H-C(7)); 7.82 (d,J=2.4, H-C(2)); 7.92 (d,J=8.8, H-C(8)); 8.41 (d,J =8.4, H-C(5)); 9.58 (s, NH). $^{13}$C-NMR (100 MHz, DMSO): 26.78; 104.72; 105.45; 118.23; 120.38; 122.95; 123.05; 123.16; 125.78; 128.17; 129.17; 129.47; 137.62; 141.50; 142.06; 143.20; 145.57; 162.88; 197.68. Anal. calc. for $C_{19}H_{14}N_2O_2 \cdot 0.3H_2O$: C 74.16, H 4.78, N 9.10; found: C 74.40, H 4.85, N 8.95.

Example 7

(E)-1-[4-(Furo[2.3-b]quinolin-4-ylamino)phenyl]ethanone oxime (compound 8a in scheme I)

To a suspension of compound 5 (61 mg, 0.20 mmol) in EtOH (5 ml), $NH_2OH \cdot HCl$ (28 mg, 0.40 mmol) was added. The mixture was heated at reflux for 30 min and allowed to cool to room temperature. The solvent was removed in vacuo, and the residue was suspended in $H_2O$ (20 ml). The precipitate obtained was collected and recrystallized from MeOH to yield the title compound 8a (63 mg, 99%).

Detected Properties of the Title Compound

M.p. 264–265° C. $^1$H-NMR (200 MHz, DMSO): 2.18 (s, Me); 6.09 (d,J=2.6, H-C(3)); 7.21 (d,J=8.8, 2 arom. H); 7.49 (m, H-C(6)); 7.71 (m, 2 arom. H, H-C(7)); 7.81 (d,J 2.6, H-C(2)); 7.91 (m, H-C(8)); 8.44 (d,J=7.6, H-C(5)); 9.60 (s, NH); 11.12 (s, NOH). $^{13}$C-NMR (50 MHz, DMSO): 11.39; 104.76; 105.73; 118.24; 121.28; 123.10; 123.21; 126.24; 128.11; 129.13; 131.74; 141.81; 142.11; 142.97; 145.62; 152.40; 162.95. Anal. calc. for $C_{20}H_{15}N_3O_2 \cdot 0.5H_2O$: C 69.98, H 4.94. N 12.88; found: C 70.36, H 4.97, N 12.66.

Example 8

(E)-1-[4-(Furo[2,3-b]quinolin-4-ylamino)phenyl]ethanone O-Methyloxime (compound 8b in scheme I)

The title compound 8b was synthesized according to the procedures as set forth in Example 7 with a yield of 99%, except that 40% $NH_2OMe \cdot HCl$ was used in place of $NH_2OH \cdot HCl$.

Detected Properties of the Title Compound

M.p. 167–168° C. $^1$H-NMR (400 MHz, DMSO): 2.19 (s, Me); 3.92 (s, MeO); 6.09 (d,J =2.8, H-C(3)); 7.19 (d,J=8.8, 2 arom. H); 7.50 (m, H-C(6)); 7.69 (m, 2 arom. H, H-C(7));

7.83 (d,J=2.8, H-C(2)); 7.91 (dd.J=8.4, 0.8. H-C(8)); 8.38 (d,J =8.4. H-C(5)); 9.52 (s. NH). $^{13}$C-NMR (100 MHz. DMSO): 12.05; 61.46; 105.12; 105.65; 118.35; 120.81; 123.02; 123.10; 126.57; 128.12; 129.12; 130.26; 141.38; 142.67; 143.14; 145.57; 153.48; 162.85. Anal. calc. for $C_{20}H_{17}N_3O_2$: C 72.49. H 5.17, N 12.68; found: C 72.33. H 5.24, N 12.53.

The configuration of the oxime moiety was determined by through-space nuclear Overhauser effect spectroscopy (NOESY), which revealed coupling connectivity to Me protons. Accordingly, (E)-1-[4-(furo[2,3-b]quinolin4-ylamino)phenyl]ethanone O-methyloxime (8b) was obtained from the reaction of compound 5 and $NH_2OMe$.

Example 9

(E)-1-[3-(Furo[2,3-b]quinolin-4-ylamino)phenyl] ethanone oxime (compound 9a in scheme I)

The title compound 9a was synthesized according to the procedures as set forth in Example 7 with a yield of 97%, except that compound 7 was used in place of compound 5.
Detected Properties of the Title Compound M.p. 248–249° C. $^1$H-NMR (200 MHz, DMSO): 2.14 (s, Me); 5.97 (d.J=2.6, H-C(3)); 7.21 (m, 1 arom. H); 7.45 (m. 3 arom. H, H-C(6)); 7.70 (m, H-C(7)); 7.77 (d,J =2.6, H-C(2)); 7.89 (dd,J =8.4, 1.0, H-C(8)); 8.42 (d,J =8.4, H-C(5)); 9.47 (s, NH); 11.22 (br. s, NOH). $^{13}$C-NMR (50 MHz, DMSO): 11.46; 103.98; 105.57; 117.87; 119.05; 120.99; 122.46; 122.95; 128.10; 129.10; 137.77; 141.50; 142.22; 142.70; 145.58; 152.51; 162.95. Anal. calc. for $C_{19}H_{15}N_3O_2$. $0.2H_2O$: C71.15, H 4.84, N 13.10; found: C71.25, H 4.89, N 12.80.

Example 10

(E)-1-[3-(Furo[2,3-b]quinolin-4-ylamino)phenyl] ethanone O-Methyloxime (compound 9b in scheme I)

The title compound 9b was synthesized according to the procedures as set forth in Example 7 with a yield of 95%, except that compound 7 and $NH_2OMe$. HCl were used in place of compound 5 and $NH_2OH$. HCl, respectively.
Detected Properties of the Title Compound M.p. 137–138° C. IH-NMR (400 MHz, DMSO): 2.18 (s, Me); 3.90 (s, MeO); 5.97 (d,J =2.8, H-C(3<<; 7.23 (m, 1 arom. H); 7.48 (m, 2 arom. H, H-C(6)); 7.56 (m, 1 arom. H); 7.71 (m, H-C(7)); 7.78 (d,J=2.8, H-C(2)); 7.90 (d, J =8.4, H-C(8)); 8.42 (d,J =8.4, H-C(5)); 9.49 (s, NH). $^{13}$C-NMR (100 MHz, DMSO): 12.27; 61.59; 104.03; 105.53; 117.88; 119.40; 121.25; 122.86; 122.93; 122.96; 128.09; 129.09; 129.15; 136.76; 141.60; 142.13; 142.75; 145.57; 153.70; 162.96. Anal. calc. for $C_{20}H_{17}N_2O_2$: C 72.49. H 5.17, N 12.68; found: C 72.36, H 5.23, N 12.60.

Example 11

1-[4-(3-Chlorofuro[2,3-b]quinolin-4-ylamino) phenyl]ethanone (compound 13 in scheme II)

Step 1. Synthesis of 3,4-dichlorofuro[2,3-b]quinoline (compound 12 in scheme II)

A mixture of 2,3,4,9-tetrahydrofuro[2,3-b]quinolin-3,4-diones (compound 11 in scheme II) (1.00 g, 5 mmOl), $POCl_3$ (30 mL) and $H_2O$ (1 mL) was heated at 110° C. for 4 h. The reaction mixture was cooled to room temperature and poured into ice-water (100 mL). A 6N NaOH solution was added until a pH of 6 was reached, and the brown precipitate was collected by suction. Purification by flash column chromatography using $CH_2Cl_2$ as elution resulted in 3,4-dichlorofuro[2,3-b]quinoline, (compound 12, 0.94 g, 79% yield).

Detected Properties of the Title Compound

M.p: 174–176° C. (lit: 118–119); $^1$H-NMR (400 MHz, DMSO-$d_6$) δ 7.78 (m, 1H), 7.91 (m, 1H), 8.09 (d, 1H, J=8.4 Hz), 8.33 (dd, 1H, J=8.4, 0.8 Hz); $^{13}$C NMR (50 MHz, DMSO-$d_6$) δ 109.59, 114.70, 123.20, 123.64, 126.80, 128.36, 130.82, 133.61, 144.58, 145.53, 158.54.

Step 2. Synthesis of 1-[4-(3-Chlorofuro[2,3-b]quinolin-4-yldmino)phenyl]ethanone (compound 13 in scheme II)

To a solution of 3,4-dichlorofuro[2,3-b]quinoline (compound 12, 0.92 g, 3.86 mmol) and 4-aminoacetophenone (0.88 g, 6.52 mmol) in EtOH (40 mL), concentrated HCl was added until a pH of 6 was reached. The mixture was refluxed for 16 h and the solvent evaporated in vacuo to yield a residual solid, which was suspended in ice-water (80 mL) and neutralized with a 1N NaOH solution. The resultant precipitate was collected by filtration, washed with $H_2O$, and then chromatographed on a column of silica gel using $CH_2Cl_2$—MeOH=10/1 to obtain the title compound 13 (0.99 g, 75% yield).
Detected Properties of the Title Compound M.p: 245–247° C. $^1$H-NMR (400 MHz, DMSO-$d_6$): δ 2.45 (s, 3H), 6.86 (d, 2H, J=8.8 Hz), 7.59 (n, 1H), 7.81 (m, 3H), 8.04 (dd, 1H, J =8.0, 0.4 Hz), 8.20 (dd, 1H, J =8.4, 0.8 Hz), 8.41 (s, 1H0, 9.52 (br s, 1H); $^{13}$C NMR (100 MHz, DMSO-$d_6$) δ 26.13, 109.79, 111.14, 122.46, 123.42, 125.01, 128.40, 128.50, 130.23, 130.28, 139.44, 143.25, 145.75, 150.85, 160.56, 195.76.

Example 12

The Production of 1-[4-(3-Chlorofuro[2,3-b] quinolin-4-ylamino)phenyl]ethanone (compound 14 in scheme II) from the hydrogenation of 1-[4-(3-Chlorofuro[2,3-b]quinolin-4-ylamino)phenyl] ethanone.

A solution of 1-[4-(3-chlorofuro[2,3-b]quinolin-4-ylamino)phenyl]ethanone (compound 13, 1.04 g, 3 mmol) in MeOH—$CH_2Cl_2$ (2/1, 30 mL) was hydrogenated for 3h under $H_2$ in the presence of 10% Pd/C (10 mg). The reaction mixture was filtered and the filtrate concentrated in vacuo to obtain a residual solid, which was chromatographed on a column of silica gel using n-hexane-EtOAc=2/1 to yield 1-[4-(3-Chlorofuro[2,3-b]quinolin-4-ylamino)phenyl] ethanone (compound 14 in scheme II)(0.72 g, 78% yield).
Detected Properties of the title Compound M.p: 222–224° C. $^1$H-NMR (400 MHz, CDCl$_3$) δ2.59 (s, 3H), 6.33 (d, 1H, J=2.8 Hz), 7.12 (d, 2H, J=8.8 Hz), 7.37 (br s, 1H), 7.48 (m, lH), 7.56 (d, 1H, J=2.6 Hz), 7.71 (m, 1H), 7.95 (d, 2H, J=8.8 Hz), 8.09 (dd, 1H, J=4.8, 0.8 Hz), 8.11 (d, 1H, J=4.8 Hz); $^{13}$C NMR (50 MHz, CDCl$_3$) δ 26.34, 105.57, 108.59, 118.19, 119.48, 121.36, 124.38, 128.77, 129.53, 130.20, 131.48, 139.01, 143.87, 145.56, 146.07, 162.66, 196.64.

Pharmacological Examples

In Vitro Anticancer Assay

All compounds were evaluated in the NCI's full panel of 60 human cancer cell lines derived from nine cancer cell types, including: leukemia (CCRF-CEM, HL-60 (TB), K-562, MOLT-4, RPMI-8226, and SR); non-small cell lung cancer (A549/ATCC, EKVX, HOP-62, HOP-92, NCI-H226, NCI-H23, NCI-H322M, and NCI-H522); colon cancer (COLO 205, HCC-2998, HCT-116, HCT-15, HT29, KMI2, and SW-620); CNS cancer (SF-268, SF-295, SF-539, SNB-19, SNB-75, and U251); melanoma (LOX IMVI, MALME- 3M, M14, SK-MEL-2, SK-MEL-28, SK-MEL-5, UACC-62, and UACC-257); ovarian cancer (IGROVI, OVCAR-3, OVCAR-4, OVCAR-5, OVCAR-8, and SK-OV-3); renal cancer (786-0, A498, ACHN, CAKI-1, RXF 393, SN12C, TK-10, and UO-31); prostate cancer (PC-3 and DU-145); and breast cancer (MCF7, MCF7/ADR-RES, MDA-MB-231/ATCC, HS 578T, MDA-MB-435, MDA-N, and T-47D).

For each compound, dose-response curves for each cell line were measured with five different drug concentrations, and the concentrations causing 50% cell-growth inhibition ($GI_{50}$) compared with the control were calculated (A. Monks, D. Scudiero, P. Skehaan, R. Shoemaker, K. Paull, D. Vistica, C. Hose, J. Langley, P. Cronise, A. Vaigro-Wolff, M. Gray-Goodrich, H. Campbell, J. Mayo, M. Boyd, *J. Natl. Cancer Inst.* 1991, 83, 757). The obtained results are listed in Table 1.

their Ac precursor (the mean $GI_{50}$ values for compounds 7, 9a and 9b are 5.27 μM, 5.60 μM and 7.56 μM, respectively). On the other hand, inthe present test, compound 4 (mean $GI_{50}$ 31.10 μM) appears to be inactive to the currently tested cancer cells lines as compared to its acridine counterpart, AHMA, which was proved to be a potent anticancer agent (T. L. Su, T. C Chou, J. Y. Kim, J. T. Huang, G. Ciszewska, W. Y. Ren, G. M. Otter, F. M. Sirotnak, K. A. Watanabe, *J. Med. Chem.* 1995, 38, 3226).

The collected results also show that compound 6 (mean $GI_{50}$=1.77 μM), with both intercalating tricyclic furo[2,3-b]quinoline and alkylating α-methylidene-γ-butyrolactone

TABLE 1

Inhibition of in vitro cancer cell lines by some 4-anilinofuro[2,3-b]quinoline derivatives ($GI_{50}$[μm][a])

|  | 4 | 5 | 6 | 7 | 8a | 8b | 9a | 9b | m-AMSA | DAM[b] |
|---|---|---|---|---|---|---|---|---|---|---|
| Leukemia | 23.02 | <0.01 | 0.90 | 3.22 | 0.14 | 0.36 | 3.64 | 4.23 | 0.10 | <0.01 |
| Non-small-cell lung cancer | 40.86 | 1.75 | 5.59 | 14.48 | 4.44 | 2.58 | 8.01 | 10.87 | 0.35 | 0.043 |
| Colon cancer | 25.16 | 0.011 | 1.56 | 5.11 | 0.17 | 0.32 | 5.35 | 6.67 | 1.07 | 0.083 |
| CNS cancer | 45.94 | 0.016 | 5.30 | 7.63 | 0.35 | 0.57 | 10.48 | 11.48 | 0.42 | 0.020 |
| Melanoma | 38.61 | 0.018 | 1.71 | 6.09 | 0.95 | 1.27 | 4.81 | 8.50 | 0.58 | 0.047 |
| Ovarian cancer | 47.72 | 0.039 | 1.92 | 11.32 | 0.53 | 0.66 | 13.57 | 11.57 | 1.05 | 0.062 |
| Renal cancer | 37.66 | 0.035 | 4.76 | 10.61 | 2.68 | 1.63 | 9.90 | 12.58 | 0.87 | 0.048 |
| Prostate cancer | 53.60 | 0.021 | 1.32 | 12.00 | 0.53 | 0.58 | 16.20 | 17.85 | 0.16 | 0.032 |
| Breast cancer | 23.85 | 0.017 | 3.27 | 5.32 | 0.42 | 0.41 | 3.62 | 8.68 | 0.58 | 0.11 |
| MG_MID[c] | 31.10 | 0.025 | 1.77 | 5.27 | 0.35 | 0.48 | 5.60 | 7.56 | 0.44 | 0.044 |

[a] Data obtained from NCI's in vitro disease-oriented tumor cells screen. $GI_{50}$: Drug molar concentration causing 50% cell growth inhibition.
[b] Daunomycin.
[c] Mean values over all cell lines tested. These cell lines are: leukemia (CCRF-CEM, HL-60 (TB), K-562, MOLT-4, PRMI-8226, and SR); non-small-cell lung cancer (A549/ATCC, EKVX, HOP-62, HOP-92, NCI-H226, NCI-H23, NCI-H322M, NCI-H460, and NCI-H522); colon cancer (COLC 205, HCC-2998, HCT-116, HCT-15, HT29, KM12, and SW-620); CNS cancer (SF-268, SF-295, SF-539, SNB-19, SNB-75, and U251); melanoma (LOX IMVI, MALME-3M, M14, SK-MEL-2, SK-MEL-28, SK-MEL-5, and UACC-257); ovarian cancer (IGROV1, OVCAR-3, OVCAR-4, OVCAR-5, OVCAR-8, and SK-OV-3); renal cancer (786-0, A498, ACHN, CAKI-1, RXF 393, SN12C, TK-10, and UO-31); prostate cancer (PC-3 and DU-145); and breast cancer (MCF7, MCF7/ADR-RES, MDA-MB-231/ATCC, HS 578T, MDA-MB-435, MDA-N and T-47D).

Compound 5 (mean $GI_{50}$=0.025 μM), which bears a 4-acetylanilino substituent at C(4) of furo[2,3-b]quinoline, was more active than its 3-acetylanilino counterpart 7 (mean $GI_{50}$=5.27 μM), and both clinically used anticancer drugs, m-AMSA (mean $GI_{50}$=0.44 μM) and daunomycin (mean $GI_{50}$ 0.044 μM).

The cytotoxicity was decreased by converting Ac group of compound 5 to the corresponding 1-(hydroxyimino)ethyl compound 8a (mean $GI_{50}$=20 0.35 μM) or 1-(methoxyimino)ethyl derivative 8b (mean $GI_{50}$=0.48 μM). The same order was obtained for 3-substituted anilinofuro[2,3-b]quinoline, in which 1-(hydroxyimino)ethyl and 1-(methoxyimino)ethyl derivatives were less active than moieties, was less active than compounds 5, 8a, and 8b. Compound 5 was capable of inhibiting all types of cancer cells tested with a mean $GI_{50}$ of less than 0.04 μM in each case except for the type of non-small-cell lung cancer (average $GI_{50}$=1.75 μM). Most of non-small-cell lung cancer cells are also resistant to compounds 8a and 8b. The inhibitory activities of compounds 5, 8a, and 8b against the individual non-small-cell-lung cancer cells are summarized in Table 2.

TABLE 2

Growth inhibition of non-small-cell lung cancer subpanels by compounds 5, 8a and 8b ($GI_{50}$ [μm])

|  | A549/ATCC | EKVX | HOP-62 | HOP-92 | NCI-H226 | NCI-H23 | NCI-H322M | NCI-H460 | NCI-H522 |
|---|---|---|---|---|---|---|---|---|---|
| 5 | 0.57 | n.d.[a] | <0.01 | 12.4 | 0.31 | 0.037 | 0.68 | 0.01 | <0.01 |
| 8a | 0.45 | 4.03 | 0.18 | 10.9 | 11.5 | 0.38 | 12.2 | 0.21 | 0.074 |
| 8b | 0.72 | 3.78 | 0.35 | 12.1 | 3.88 | 0.57 | 1.22 | 0.56 | <0.01 | n.d.[a] = Not determined.

Although non-small-cell-lung cancer is resistant to compound 5 with an average Glso value of 1.75 μM, the sensitivity within this type of cancer cells varies; HOP-62 ($GI_{50}$<0.01 μM), NCI-H460 ($GI_{50}$=0.01 μM), and NCI- H522 (GI$_{50}$<0.01 μM) are very sensitive, while HOP-92 (GI$_{50}$=12.4 μM) is resistant. Among these cancer cells, NCI-H522 was found to be very sensitive to compounds 5, 8a, and 8b with GI$_{50}$ values of less than 0.01 μM, 0.074 μM and <0.01 μM, respectively.

All patents and literature references cited in the present specification are hereby incorporated by reference in their entirety. In case of conflict, the present description, including definitions, will prevail.

While the invention has been described with reference to the above specific embodiments, it is apparent that numerous modifications and variations can be made without departing from the scope and spirit of this invention. It is therefore intended that this invention be limited only as indicated by the appended claims.

I claim:

1. A compound of formula (I) or a pharmaceutically acceptable salt thereof:

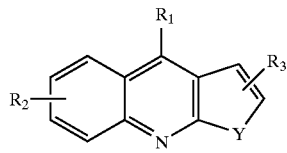

wherein

Y represents S O or NH;

R$_1$ represents a group selected from the group consisting of:

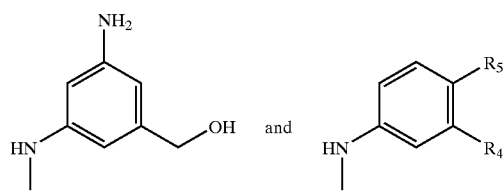

wherein

R$_4$ represents: H or

wherein X represents O, S, NH or NOR, R in NOR being H or a C$_1$–C$_4$ alkyl group, and R$_6$ represents H or a C$_1$–C$_4$ alkyl group;

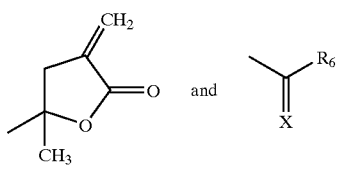

R$_5$ is selected from the group consisting of H, wherein X represents O, S, NH or NOR, R in NOR being H or a C$_1$–C$_4$ alkyl group, and R$_6$ represents H or a C$_1$–C$_4$ alkyl group;

with the proviso that one of R$_4$ and R$_5$ is H;

R$_2$ represents: H, halogen, a C$_1$–C$_4$ alkyl group, hydroxyl, a C$_1$–C$_4$ alkoxy group, nitro or amino; and R$_3$ represents: H, halogen, a C$_1$–C$_4$ alkyl group, hydroxyl, a C$_1$–C$_4$ alkoxy group, nitro or amino.

2. The compound of claim 1, wherein Y is O.

3. The compound of claim 1, wherein R$_1$ is

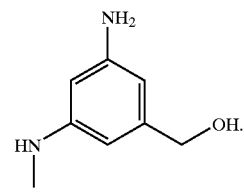

4. The compound of claim 1, wherein R$_1$ is

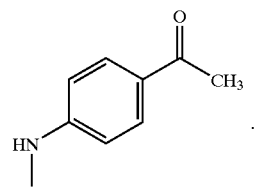

5. The compound of claim 1, wherein R$_1$ is

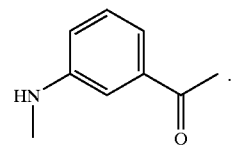

6. The compound of claim 1, wherein R$_1$ is

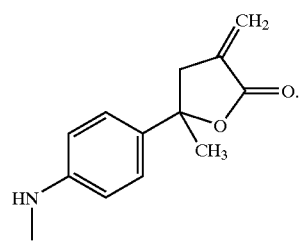

7. The compound of claim 1, wherein R$_1$ is

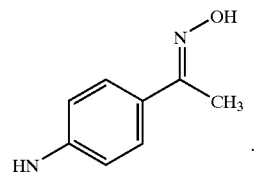

8. The compound of claim 1, wherein R$_1$ is

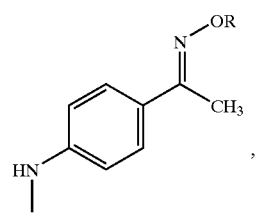

and R is H or methyl.

9. The compound of claim 1, wherein $R_1$ is

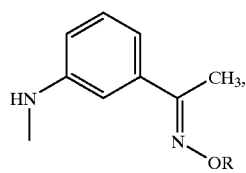

and R is H or methyl.

10. The compound of claim 1, wherein $R_2$ is H.

11. The compound of claim 1, wherein $R_3$ is H.

12. A pharmaceutical composition comprising a compound of formula (I) as claimed in claim 1 or a pharmaceutically acceptable salt thereof, and, optionally, a pharmaceutically acceptable carrier.

13. A pharmaceutical composition for inhibiting of growth of a tumor/cancer cell selected from the group consisting of leukemia cancer cells, non-small-lung cancer cells, colon cancer cells, CNS cancer cells, melanoma cancer cells, ovarian cancer cells, renal cancer cells, prostate cancer cells, breast cancer cells, and combinations thereof, comprising a compound of formula (I) as claimed in claim 1 or a pharmaceutically acceptable salt thereof, and, optionally, a pharmaceutically acceptable carrier.

14. A method for producing a compound for inhibiting the growth of a tumor/cancer cell. the compound of formula (I'):

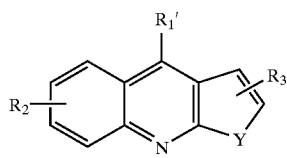

wherein

Y represents: S, O or NH;

$R_1$ represent a group selected from the group consisting of:

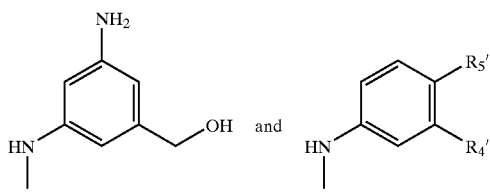

wherein one of $R_4'$ and $R_5'$ is H, and the other is

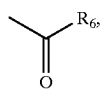

wherein $R_6$ represents H or a $C_1$–$C_4$ alkyl group;

$R_2$ represents; H, halogen, a $C_1$–$C_4$ alkyl group, hydroxyl, a $C_1$–$C_4$ alkoxy group, nitro or amino; and $R_3$ represents; H, halogen, a $C_1$–$C_4$ alkyl group, hydroxyl, a $C_1$–$C_4$ alkoxy group, nitro or amino;

the process comprising the step of reacting a compound of formula (A):

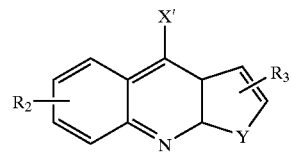

(A)

wherein $R_2$, $R_3$ and Y are the same as those defined for formula (I'); and

X' represents Cl, Br or I;

with a compound selected from the group consisting of a compound of the formula

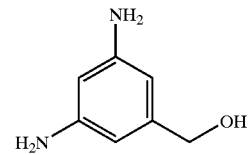

and a compound of formula

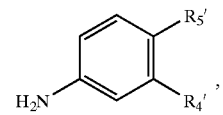

wherein $R_4'$ and $R_5'$ are the same as those defined for formula (I').

15. The process as claimed in claim 14, wherein the compound of formula (A) is reacted with the compound of formula

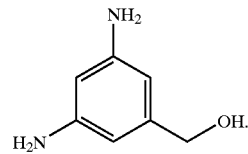

16. The process as claimed in claim 14, wherein the compound of formula (A) is reacted with the compound of formula

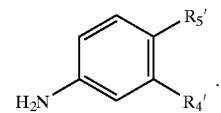

17. The process as claimed in claim 16, wherein the compound of formula

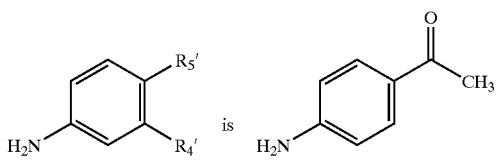

18. The process as claimed in claim 16, wherein the compound of formula

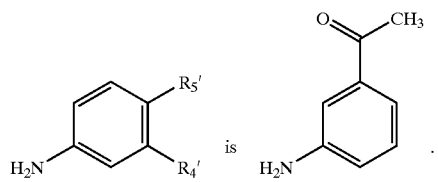

is

19. The process as claimed in claim 16, wherein the resultant compound of formula (I') is further treated with a compound of formula NH$_2$OR, R being H or a C$_1$–C$_4$ alkyl group, such that the

group in the

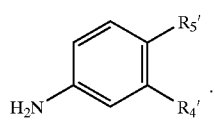

group of said compound of formula (I') is chemically modified to a

group wherein R is H or a C$_1$–C$_4$ alkyl group.

20. The process as claimed in claim 16, wherein the resultant compound of formula (I') is further treated with a Lawesson's reagent or P$_2$S$_2$, such that the

group in the

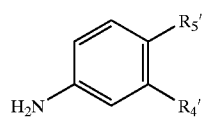

group of said compound of formula (I') is chemically modified to a

group.

21. The process as claimed in claim 16, wherein the resultant compound of formula (I') is further treated with benzyldimethylphosphinimide, such that the

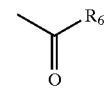

group in the

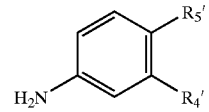

group of said compound of formula (I') is chemically modified to a

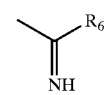

group.

22. The process as claimed in claim 16, wherein the compound of formula

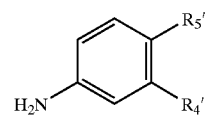

is one where R$_4$' is H and R$_5$' is

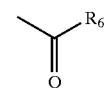

23. The process as claimed in claim 22, wherein the resultant compound of formula (I') is further treated with a compound of formula NH$_2$OR, R being H or a C$_1$–C$_4$ alkyl group, such that the

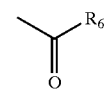

group in said compound of formula (I') is chemically modified to a

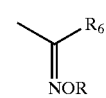

group, wherein R is H or a C$_1$–C$_4$ alkyl group.

24. The process as claimed in claim 22, wherein the resultant compound of formula (I') is further treated with ethyl α-bromomethyl acrylate, such that the

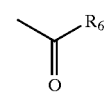

group in said compound of formula (I') is chemically modified to a group of formula

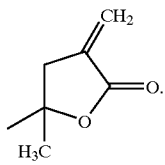

25. The process as claimed in claim 14, wherein the compound of formula (A) is a compound of

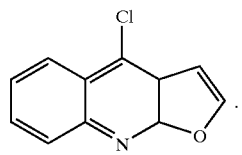

26. The process as claimed in claim 25, wherein the compound of the formula

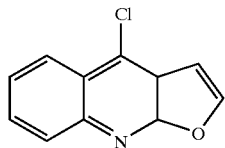

is produced by a process comprising the steps of:

(a) forming a compound of formula

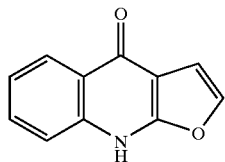

from the reaction of a compound of formula

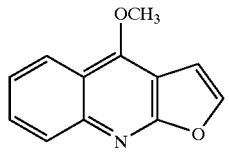

with HBr; and (b) reacting the resultant compound of

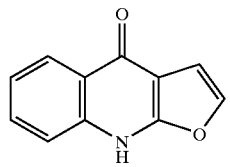

from step (a) with $POCl_3$.

27. The process as claimed in claim 14, wherein the compound of formula (A) is compound of formula

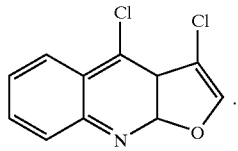

28. The process as claimed in claim 27, wherein the compound of formula

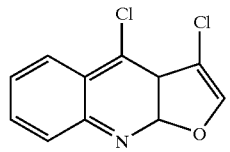

is formed from the reaction of a compound of formula

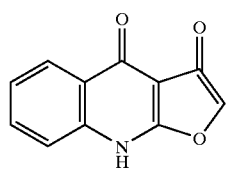

and $POCl_3$.

29. The process as claimed in claim 27, wherein the resultant compound of formula (I') is further subjected to a hydrogenation reaction in the presence of Pd/C in $CH_2Cl_2$ to thereby form a compound of formula

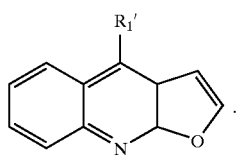

* * * * *